(12) United States Patent
Lietzau

(10) Patent No.: US 10,809,522 B2
(45) Date of Patent: Oct. 20, 2020

(54) ENDOSCOPE

(71) Applicant: Scholly Fiberoptic GmbH, Denzlingen (DE)

(72) Inventor: Thomas Lietzau, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 574 days.

(21) Appl. No.: 15/223,489

(22) Filed: Jul. 29, 2016

(65) Prior Publication Data

US 2017/0168287 A1    Jun. 15, 2017

(30) Foreign Application Priority Data

Dec. 10, 2015    (DE) .................. 10 2015 015 993

(51) Int. Cl.
| | | |
|---|---|---|
| *A61B 1/07* | (2006.01) | |
| *A61B 1/06* | (2006.01) | |
| *A61B 1/04* | (2006.01) | |
| *G02B 23/24* | (2006.01) | |
| *A61B 1/00* | (2006.01) | |

(52) U.S. Cl.
CPC ........ *G02B 23/2492* (2013.01); *A61B 1/0011* (2013.01); *A61B 1/00108* (2013.01); *A61B 1/042* (2013.01); *A61B 1/0623* (2013.01); *A61B 1/0669* (2013.01); *A61B 1/07* (2013.01); *G02B 23/2453* (2013.01); *G02B 23/2469* (2013.01); *G02B 23/2484* (2013.01)

(58) Field of Classification Search
CPC ............ G02B 23/2492; G02B 23/2453; G02B 23/2469; G02B 23/2484; A61B 1/00108; A61B 1/0011; A61B 1/042; A61B 1/0623; A61B 1/0669; A61B 1/07
USPC ....... 600/109, 112, 132, 133, 138, 139, 140, 600/160, 182
See application file for complete search history.

(56) References Cited

U.S. PATENT DOCUMENTS

| | | | |
|---|---|---|---|
| 6,503,196 B1 | 1/2003 | Kehr et al. | |
| 2011/0196355 A1* | 8/2011 | Mitchell | ............... A61B 34/25 606/11 |
| 2013/0102846 A1* | 4/2013 | Sjostrom | .................. A61B 1/07 600/110 |

(Continued)

FOREIGN PATENT DOCUMENTS

| | | |
|---|---|---|
| DE | 10359337 | 8/2005 |
| DE | 102013110587 | 4/2015 |
| WO | 9916341 | 4/1999 |

*Primary Examiner* — Timothy J Neal
*Assistant Examiner* — William B Chou
(74) *Attorney, Agent, or Firm* — Volpe and Koenig, P.C.

(57) ABSTRACT

The electronic endoscope has an endoscope shaft (2) and an electronics housing (3), and also an optical waveguide (5) having optical fibers (4). The endoscope shaft (2) is formed on the electronics housing (3) or connected thereto, the electronics housing (3) being closed so as to be vapor-tight and liquid-tight from outside. The optical waveguide (5) extends between a distal end (6) of the endoscope shaft (2), directed away from the electronics housing (3), and a light source (7) arranged in the electronics housing (3). The optical waveguide (5) has, at its proximal end (8), an optical waveguide connector (9), with which a light exit point (10) from the electronics housing (3) is closed off in a vapor-tight and liquid-tight manner.

18 Claims, 3 Drawing Sheets

(56) References Cited

U.S. PATENT DOCUMENTS

2014/0031726 A1\* 1/2014 Chernomorsky ...... A61B 17/24
                                                    601/2
2015/0087998 A1    3/2015 Czupalla et al.
2018/0214210 A1\* 8/2018 Mitchell ................ A61B 34/25

\* cited by examiner

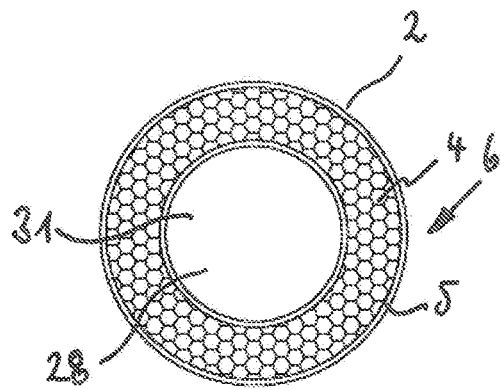
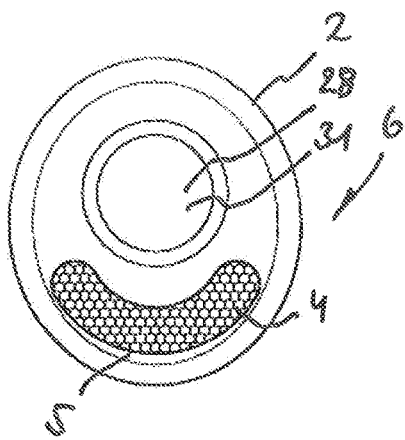
Fig. 4　　　　　　　　Fig. 5
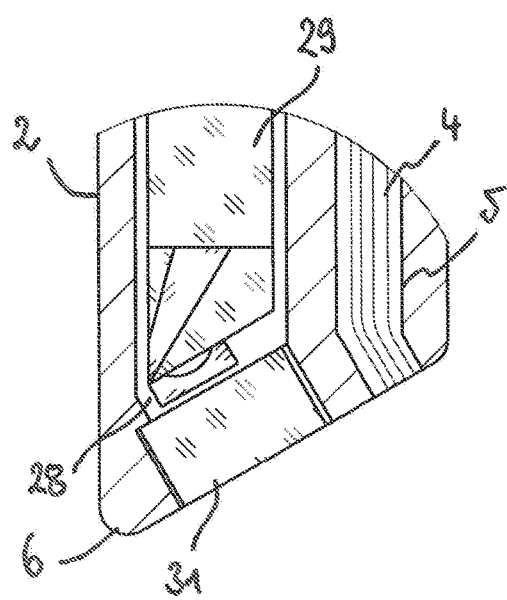
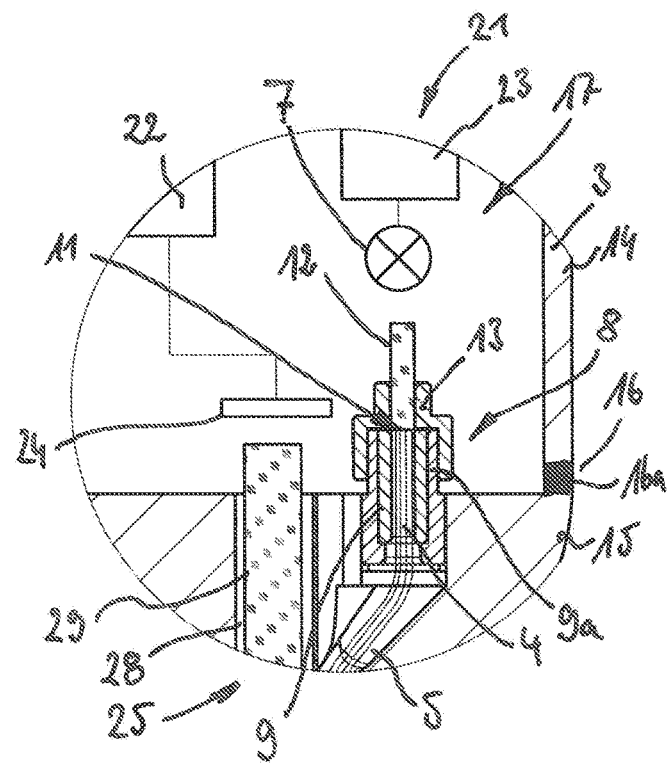
Fig. 6　　　　　　　　Fig. 7

ENDOSCOPE

INCORPORATION BY REFERENCE

The following documents are incorporated herein by reference as if fully set forth: German Patent Application No. 102015015993.3, filed Dec. 10, 2015.

BACKGROUND

The invention relates to an endoscope with an endoscope shaft, with an electronics housing, and with an optical waveguide comprising optical fibers, the endoscope shaft being formed on the electronics housing or connected thereto, the electronics housing being closed so as to be vapor-tight and liquid-tight from outside, and the optical waveguide extending between a distal end of the endoscope shaft, directed away from the electronics housing, and a light source arranged in the electronics housing. Light for illuminating and taking images of an examination space can be introduced into the examination space via the optical waveguide.

Endoscopes of this kind are known from practice and have the advantage that their electronics arranged inside the electronics housing can remain on the endoscope during a treatment of the endoscope, since they are closed off from the external environment in a vapor-tight and liquid-tight manner. Undesired entry of vapor into the electronics housing, for example during the autoclaving of these endoscopes, can thus be prevented. However, in connection with endoscopes of this kind, it has proven problematic that vapor and/or liquid can penetrate the electronics housing via the optical waveguide with the optical fibers. To avoid this, it has hitherto been proposed for the optical waveguide to be sealed off at its distal end, for example by suitably tight attachment lenses.

However, a difficulty that arises in sealing off the optical waveguide with attachment lenses is that attachment lenses of this kind can generate undesired reflections, which can make it difficult to obtain perfect optical imaging with the endoscope. Moreover, such attachment lenses are expensive to produce and to assemble.

SUMMARY

The object of the invention is therefore to make available an endoscope which is of the type defined at the outset and which is easier to produce.

To achieve this object, an endoscope having one or more features of the invention is provided. In particular, in an endoscope of the type defined at the outset, it is thus proposed that the optical waveguide has, at its proximal end, an optical waveguide connector, with which a light exit point on the electronics housing is closed off in a vapor-tight and liquid-tight manner. In this way, a sealing point for sealing off the optical waveguide and therefore for sealing off the electronics housing can be routed from the distal end of the endoscope shaft to the proximal end of the optical waveguide. Due to the space conditions existing there, it is thus possible to provide reliable sealing of the light exit point from the electronics housing, which sealing can be produced at less cost.

To further simplify the sealing of the light exit point, provision can be made that the optical fibers, at their proximal ends, are bonded to one another and ground. Moreover, it is possible that a light-guiding element is mounted on the proximal ends of the optical fibers, which light-guiding element reliably transmits light, emitted from the light source, to the optical fibers of the optical waveguide. This light-guiding element can be, for example, a glass body, preferably a glass rod, which bridges the distance between the light source and the optical waveguide connector.

The bonding and grinding of the proximal ends of the optical fibers can, on the one hand, favor the transfer of light from the light-guiding element into the optical fibers, while at the same time, on the other hand, the sealing of the light exit point from the electronics housing by means of the optical waveguide connector can be simplified and thus improved.

It is possible for the optical fibers also to be bonded together and ground at their distal ends.

The light-guiding element can be held in a sleeve of the optical waveguide connector in a vapor-tight and liquid-tight manner. It is possible to connect the sleeve in a vapor-tight and liquid-tight manner to the electronics housing and/or to a connector sleeve of the optical waveguide connector, in order to prevent undesired entry of vapor and/or liquid through the connection point between the sleeve and the connector sleeve of the optical waveguide connector or the electronics housing. Particularly preferably, the sleeve can be connected in a vapor-tight and liquid-tight manner to the electronics housing and/or to the connector sleeve of the optical waveguide connector, if a cohesive connection is provided for this purpose, preferably by welding, adhesive bonding and/or soldering.

To be able to produce a vapor-tight and liquid-tight connection also between the light-guiding element and the sleeve in a particularly uncomplicated way, it may be expedient if the sleeve is made of metal or has at least one metallized surface directed toward the light-guiding element, and/or the light-guiding element has a metallic coating. In this way, it is possible to connect the sleeve to the light-guiding element in a vapor-tight and liquid-tight manner, in particular to connect it cohesively. For this purpose, the sleeve and the light-guiding element can be welded, adhesively bonded and/or soldered to each other.

For the vapor-tight and liquid-tight connection between the light-guiding element and the sleeve, the metallic layer can be applied to the light-guiding element for example by means of sputtering. The light-guiding element thus metallized can then be inserted into the sleeve, which for its part is made of metal or metallized, and can be soldered or welded there.

The sealing, according to the invention, of the light exit point from the electronics housing of the endoscope according to the invention means that the endoscope, in particular the optical waveguide, can be designed without an attachment lens at its distal end of the optical waveguide.

In a further embodiment of the endoscope according to the invention, which embodiment is possibly of independent inventive merit, provision can be made that the electronics housing of the endoscope comprises at least two housing parts. The electronics housing and its two housing parts can preferably be made of metal.

To produce vapor-tight and liquid-tight sealing of the electronics housing from the outside, provision is preferably made that the at least two housing parts of the electronics housing are connected to each other in a vapor-tight and liquid-tight manner. This can be done, for example, by a cohesive connection of the two housing parts. Preferably, the at least two housing parts of the electronics housing can be adhesively bonded, welded or soldered. Particularly if the electronics housing and its at least two housing parts are made of metal, at least at the joints, it is also possible for the at least two housing parts to be welded to each other, thus providing a particularly durable vapor-tight and liquid-tight connection of the housing parts.

If one housing part of at least two housing parts of the electronics housing contains electronics of the endoscope, and the optical waveguide connector and the endoscope shaft are provided on another housing part of at least two housing parts of the electronics housing, maintenance and/or repair of the endoscope according to the invention can be made easier. In the case of maintenance, the connection between the two housing parts of the electronics housing can be separated. In one of the housing parts, the electronics of the endoscope can then be accessed, while all the components of the endoscope pertaining to the shaft, i.e. the endoscope shaft and also the optical waveguide and the optical waveguide connector according to the invention, are accessible in the other housing part.

In one embodiment of the endoscope according to the invention, provision is made that the electronics housing has a vapor-tight and liquid-tight passage for a data and/or power cable. In this way, it is possible, on the one hand, to transmit data from the individual electronic components of the endoscope, in particular image data, by cable to a receiver unit, and, on the other hand, to ensure vapor-tight and liquid-tight sealing of the electronics housing, so as to protect the components arranged inside the electronics housing from contact with vapor and/or liquid.

In another embodiment of the endoscope according to the invention, provision can additionally or alternatively be made that the electronics housing accommodates means for wireless data transmission, in particular for wireless transmission of image data.

Particularly if an endoscope is wanted that is completely free of cables, it may be expedient if the electronics housing accommodates a power store. Such a power store can be an accumulator and/or a battery, for example. In this context, it may be particularly expedient if the endoscope has, in particular on the electronics housing, a charging interface which is connected to the power store of the electronics housing and is accessible from the outside. Thus, the power store inside the electronics housing can be recharged from time to time, without the electronics housing having to be opened. A wireless endoscope of this kind is distinguished in particular by its comfortable handling.

In one embodiment of the endoscope according to the invention, provision can be made that the endoscope has an image sensor which, sealed off in a vapor-tight and liquid-tight manner, is arranged in a distal end of the endoscope shaft. By contrast, in another embodiment of the endoscope according to the invention, provision can be made that the endoscope has an image sensor which, sealed off in a vapor-tight and liquid-tight manner, is arranged in the electronics housing and in this case preferably adjacent to a proximal end of the endoscope shaft.

It will be noted that electronics arranged in the electronics housing can comprise at least processing electronics for image data of an image sensor, for example of the aforementioned image sensor, and/or control electronics for the light source. An LED, for example, can be used as a suitable light source.

Transmission of an image from an examination space into the electronics housing can take place electronically, or also optically via an optical channel in the endoscope shaft. Particularly in the case of an image sensor in the distal end of the endoscope shaft, it is expedient for the image to be transmitted from the examination space electronically. In an arrangement with an image sensor at the proximal end of the endoscope shaft inside the electronics housing, it may be expedient for the transmission to take place optically via an optical channel.

The sealing of the light exit point with the optical waveguide connector can be of such quality that the endoscope according to the invention is able to be autoclaved without vapor and/or liquid penetrating the electronics housing.

WO 99/16341 A1 discloses an optical waveguide which can be connected to a cold-light source by a connector. However, compared to the endoscope according to the invention, the optical waveguide in said document is not inserted into an electronics housing of the endoscope closed off in a vapor-tight manner.

BRIEF DESCRIPTION OF THE DRAWINGS

Illustrative embodiments of the invention are described in more detail below with reference to the drawing, parts of which are highly schematic and in which:

FIG. 4 shows a front view of a possible illustrative embodiment of a shaft tube of an endoscope according to the invention, wherein an optical channel, sealed off by means of a plane glass, and the distal end of the optical waveguide with the optical fibers can be seen, wherein the distal end of the optical waveguide has no attachment lens and is therefore not sealed off, FIG. 5 shows another front view of a distal end of an endoscope shaft according to the invention with an optical channel, sealed off by a plane glass, and with an optical waveguide which concentrically surrounds the optical channel and which has a large number of optical fibers, wherein the distal end of the optical waveguide has no attachment lens and is therefore not sealed off, FIG. 6 shows an enlarged view of the detail labeled by the circle K1 in FIGS. 2 and 3, and FIG. 7 shows an enlarged view of the detail labeled by the circle K2 in FIGS. 2 and 3.

DETAILED DESCRIPTION OF THE PREFERRED EMBODIMENT

In the following description of various embodiments of the invention, elements that correspond in terms of their function retain corresponding reference numbers even when their configuration or shape differs.

Figure 1:
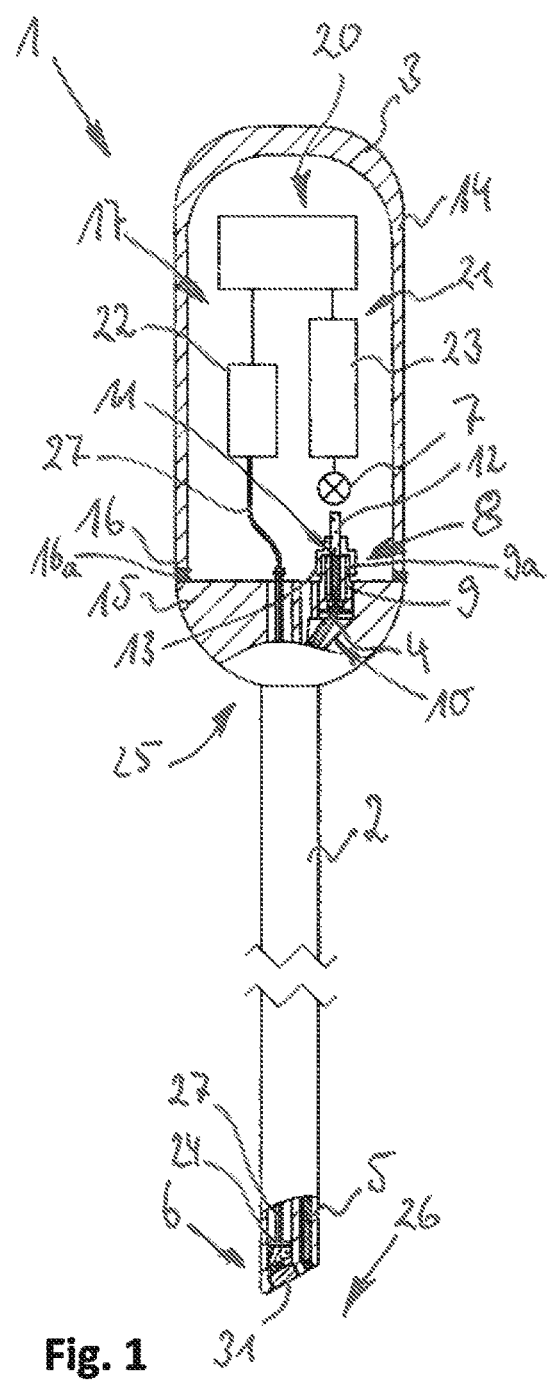
FIG. 1 shows a sectional side view of a first illustrative embodiment of an endoscope according to the invention, wherein the sealing optical waveguide connector can be seen in the interior of the electronics housing, and an image sensor can be seen in the distal end of the endoscope shaft.
Figure 2:
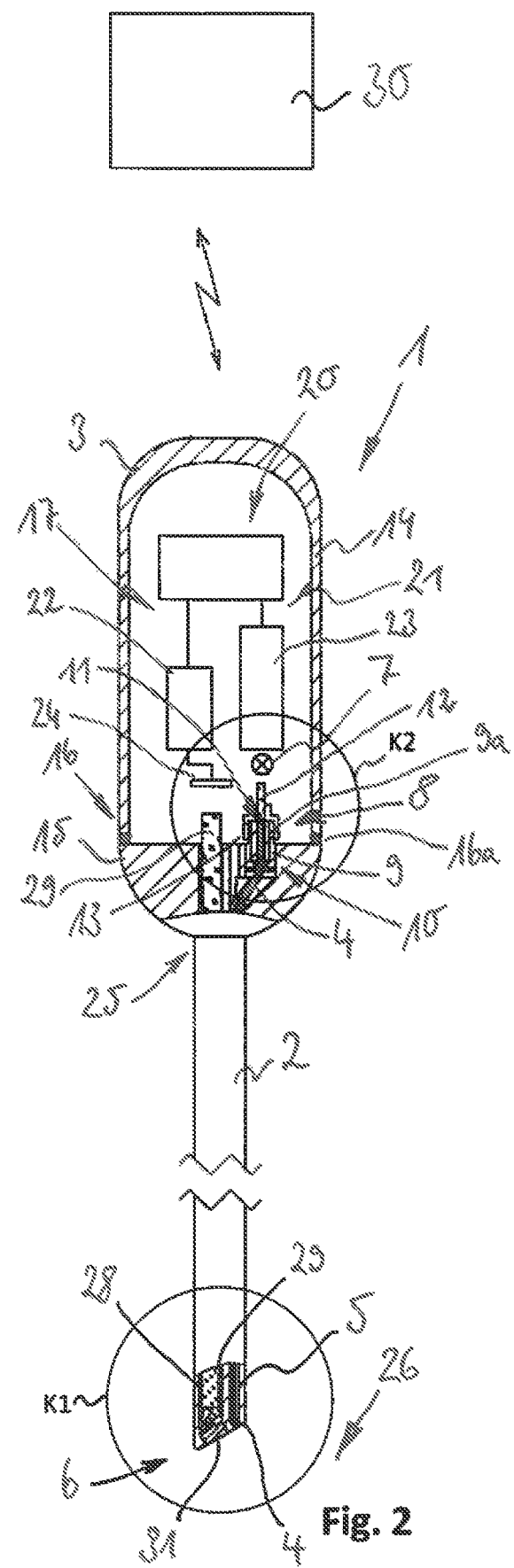
FIG. 2 shows a sectional side view of a second embodiment of a cableless endoscope according to the invention, wherein an image sensor can be seen here in the interior of the electronics housing, which image sensor receives its image information via an optical channel formed inside the endoscope shaft.
Figure 3:
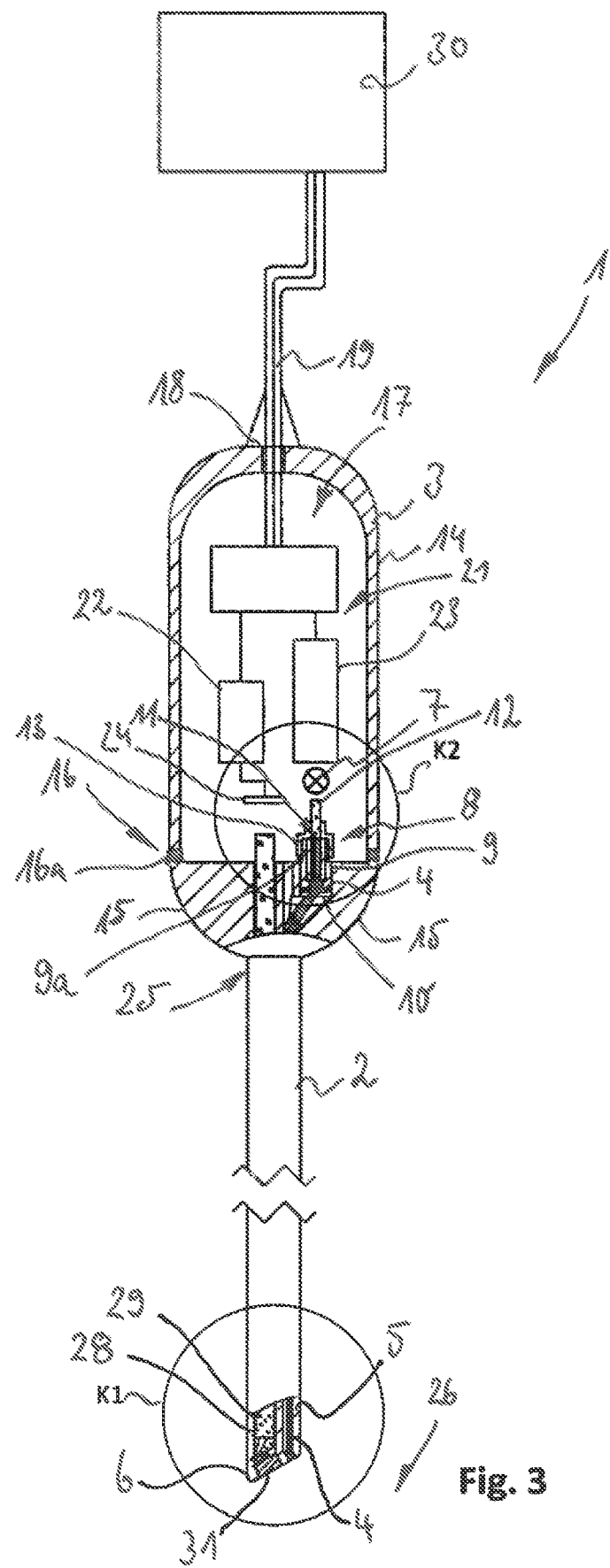
FIG. 3 shows a sectional side view of a third embodiment of an endoscope according to the invention, wherein the endoscope is connected to a control unit via a supply line.

FIGS. 1 to 3 show three different embodiments of an electronic endoscope, designated overall by reference sign 1. Each of the endoscopes 1 is equipped with an endoscope shaft 2, with an electronics housing 3, and with an optical waveguide 5 comprising optical fibers 4. The endoscope shaft 2 is formed on the electronics housing 3 or connected thereto. The electronics housing 3 is closed so as to be vapor-tight and liquid-tight from outside. The optical waveguide 5 extends between a distal end 6 of the endoscope shaft 2, directed away from the electronics housing 3, and a light source 7 arranged in the electronics housing 3.

At its proximal end 8, the optical waveguide 5 has an optical waveguide connector 9, with which a light exit point 10 from the electronics housing 3 is closed off in a vapor-tight and liquid-tight manner.

The optical fibers 4, at their proximal ends 11, are bonded to one another and ground. A light-guiding element 12, here in the form of a glass rod, is mounted on the bonded-together and ground proximal ends 11 of the optical fibers 4. The light-guiding element 12 serves to ensure that light emitted from the light source 7 is transmitted to the optical fibers 4 of the optical waveguide 5. Moreover, the light-guiding element 12 also has a sealing function which prevents vapor and/or liquid from entering the interior of the electronics housing 3 via the light exit point 10, particularly when the electronic endoscope 1 is being autoclaved.

For this purpose, the light-guiding element 12 is held in a vapor-tight and liquid-tight manner in a sleeve 13 of the optical waveguide connector. The sleeve 13 is connected in a vapor-tight and liquid-tight manner to a connector sleeve 9a of the optical waveguide connector 9, such that neither vapor nor liquid can enter the interior of the electronics housing 3 at this point too. For this purpose, the sleeve 13 and the connector sleeve 9a of the optical waveguide connector 9 are connected cohesively to each other. This can be done, for example, by welding, adhesive bonding or soldering.

To be able to produce a cohesive connection between the sleeve 13 and the light-guiding element 12 designed as a glass rod, the light-guiding element 12 has a metallic coating, i.e. is metallized. The sleeve 13 for its part is produced from metal or is likewise provided with a metallic coating. The light-guiding element 12 and the sleeve 13 are connected to each other in a vapor-tight and liquid-tight manner, specifically in a cohesive connection. The cohesive connection of the light-guiding element 12 to the sleeve 13 can be produced by welding, adhesive bonding or soldering.

The figures show that the electronics housing 3 of the endoscopes 1 shown in the figures comprises two housing parts 14 and 15. At least at a join 16 between the two housing parts 14 and 15, the latter are made of metal. Here, a weld seam 16a can be seen in the figures. The two housing parts 14 and 15 of the electronics housing 3 are cohesively connected to each other in a vapor-tight and liquid-tight manner. In the present illustrative embodiment, the two housing parts 14 and 15 of the endoscope according to the invention are welded to each other. However, it is also conceivable for the two housing parts 14 and 15 of the electronics housing 3 to be adhesively bonded or soldered to each other.

The housing part 14 of the two housing parts 14 and 15 of the electronics housing 3 contains the electronics 17 of the endoscope 1. The optical waveguide connector 9 and the endoscope shaft 2 are arranged on the other housing part 15.

The endoscope 1 shown in FIG. 3 has an electronics housing 3 with a vapor-tight and liquid-tight passage 18 for a data and/or power cable 19, which can also be designated as supply line.

In the two endoscopes 1 shown in FIGS. 1 and 2, the electronics housing 3 accommodates means 20 for wireless data transmission, in particular of image data. Moreover, the electronics housings 3 of these two endoscopes 1 each accommodate a power store 21, for example in the form of an accumulator and/or a battery. To charge the power store 21 in the interior of the electronics housing 3, the endoscopes 1 can have a charging interface which is connected or connectable to the power store 21 and is preferably accessible from the outside.

The endoscope 1 shown in FIG. 3 is connected by the data and/or power cable 19 to a receiver unit 30, from which it obtains energy and to which it transmits image data. The two endoscopes 1 of FIGS. 1 and 2 communicate wirelessly with a correspondingly configured receiver unit 30 via the means 20.

Inside their electronics housings 3, all of the endoscopes 1 have an image data processor 22 and control electronics 23 for the light source 7 assigned to the optical waveguide 5. Moreover, each of the endoscopes 1 is provided with an image sensor 24 which, sealed off in a vapor-tight and liquid-tight manner, is arranged either in a distal end 6 of the endoscope shaft 2, as in the endoscope 1 according to FIG. 1, or in the electronics housing 3, adjacent to a proximal end 25 of the endoscope shaft 2, as in the two endoscopes 1 shown in FIGS. 2 and 3.

Transmission of an image from an examination space 26 into the electronics housing 3 takes place in two different ways in the endoscopes shown in FIGS. 1 to 3. In the case of an image sensor 24 arranged in the distal end 6 of the endoscope shaft 2, as is provided in the configuration of the endoscope 1 shown in FIG. 1, the transmission of the image, generated by the image sensor 24, from the examination space 26 into the electronics housing 3 takes place electronically via a cable 27 running in the interior of the endoscope shaft 2, which cable 27 is connected in the interior of the electronics housing 3 to the image data processor 22.

In the illustrative embodiments of the endoscope 1 according to FIGS. 2 and 3, the transmission of an image from the examination space 26 takes place optically via an optical channel 28, which reaches from the distal end 6 of the endoscope shaft 2 to the interior of the electronics housing 3 and to the image sensor 24 arranged at the proximal end 25 of the endoscope shaft 2. Inside the optical channel 28, an optical transmission element 29 is provided with which the light emitted from the examination space 26 can be fed to the image sensor 24 arranged inside the electronics housing 3.

FIGS. 4 and 5 show two different embodiments of endoscope shafts 2 according to the invention. In the endoscope shaft 2 shown in FIG. 4, an annular optical waveguide 5 concentrically surrounds the optical channel 28. The optical channel 28 and the optical transmission element 29 arranged therein are closed in a vapor-tight and liquid-tight manner by a plane glass 31, such that entry of vapor and liquid through the optical channel 28 into the interior of the electronics housing 3 can be avoided. On account of the proximal sealing of the optical waveguide 5 by the optical waveguide connector 9, the optical waveguide 5 can be designed without an attachment lens at the distal end, such that here the optical fibers 4 are uncovered. This is able to promote good radiation of the light from the optical fibers 4 into the examination space 26.

In the endoscope shaft 2 shown in FIG. 5, the optical waveguide 5 and its optical waveguide channel have a cross section in the shape of an arc of a circle. Here too, the optical channel 28 is closed tightly with a plane glass 31, while the optical waveguide 5 and the optical fibers 4 are without an attachment lens.

The electronic endoscope has the endoscope shaft 2 and the electronics housing 3, and also the optical waveguide 5 comprising optical fibers 4. The endoscope shaft 2 is formed on the electronics housing 3 or connected thereto, said electronics housing 3 being closed so as to be vapor-tight and liquid-tight from outside. The optical waveguide 5 extends between the distal end 6 of the endoscope shaft 2, directed away from the electronics housing 3, and the light source 7 arranged in the electronics housing 3. The optical waveguide 5 has, at its proximal end 8, the optical waveguide connector 9, with which the light exit point 10 from the electronics housing 3 is closed off in a vapor-tight and liquid-tight manner.

LIST OF REFERENCE SIGNS 1 electronic endoscope
2 endoscope shaft
3 electronics housing
4 optical fibers
5 optical waveguide
6 distal end of 2
7 light source
8 proximal end of 5
9 optical waveguide connector
9a connector sleeve
10 light exit point
11 proximal ends of 4
12 light-guiding element
13 sleeve
14 housing part
15 housing part
16 join between 14 and 15
16a weld seam
17 electronics
18 passage for 19
19 supply line
20 means for wireless data transmission
21 power store
22 image data processor
23 control electronics
24 image sensor
25 proximal end of 2
26 examination space
27 cable
28 optical channel
29 optical transmission element
30 receiver unit
31 plane glass

The invention claimed is:

1. An endoscope (1) comprising an endoscope shaft (2), an electronics housing (3), and an optical waveguide (5) comprising optical fibers (4), the endoscope shaft (2) being formed on the electronics housing (3) or connected thereto, the electronics housing (3) being closed vapor-tight and liquid-tight from outside, and the optical waveguide (5) extending between a distal end (6) of the endoscope shaft (2), opposite from the electronics housing (3), and a light source (7) arranged in the electronics housing (3), the optical waveguide (5) has, at a proximal end (8) thereof, an optical waveguide connector (9), with which a light exit point (10) from the electronics housing (3) to the endoscope shaft (2) is closed off in a vapor-tight and liquid-tight manner, the optical fibers are sealed to one another by bonding at the proximal end, wherein the electronics housing (3) comprises at least two housing parts (14, 15), and one housing part (14) of the at least two housing parts (14, 15) contains electronics (17) of the endoscope (1), and the optical waveguide connector (9) and the endoscope shaft (2) are provided on another housing part (15) of the at least two housing parts (14, 15) of the electronics housing (3).

2. The endoscope (1) as claimed in claim 1, wherein the optical fibers (4), at proximal ends (11) thereof, are bonded to one another and ground.

3. The endoscope (1) as claimed in claim 2, wherein a light-guiding element (12) is mounted on the proximal ends (11) of the optical fibers (4).

4. The endoscope (1) as claimed in claim 3, wherein the optical waveguide connector (9) has a sleeve (13) in which the light-guiding element (12) is held in a vapor-tight and liquid-tight manner.

5. The endoscope (1) as claimed in claim 4, wherein the sleeve (13) is connected in a vapor-tight and liquid-tight manner to at least one of the electronics housing (3) or a connector sleeve (9a) of the optical waveguide connector (9).

6. The endoscope (1) as claimed in claim 5, wherein the sleeve (13) is connected cohesively to at least one of the electronics housing (3) or the connector sleeve (9a).

7. The endoscope (1) as claimed in claim 4, wherein the light-guiding element (12) has a metallic coating, the sleeve (13) has at least one metallized surface directed toward the light-guiding element (12) in a position of use or is made of metal, and the light-guiding element (12) and the sleeve (13) are connected to each other in a vapor-tight and liquid-tight manner.

8. The endoscope (1) as claimed in claim 7, wherein the light-guiding element (12) and the sleeve (13) are connected to each other by a welded, adhesively bonded, or soldered connection.

9. The endoscope (1) as claimed in claim 1, wherein the electronics housing (3) comprises the at least two housing parts (14, 15) that are made of metal at least at a joint (16), and the at least two housing parts (14, 15) are connected to each other in a vapor-tight and liquid-tight manner.

10. The endoscope (1) as claimed in claim 9, wherein the at least two housing parts (14, 15) are connected to each other by a welded, adhesively bonded or soldered connection.

11. The endoscope (1) as claimed in claim 1, wherein the electronics housing (3) has a vapor-tight and liquid-tight passage (18) for at least one of a data or power cable (19).

12. The endoscope (1) as claimed in claim 1, further including at least one of means (20) for wireless data transmission or a power store (21) in the electronics housing (3).

13. The endoscope (1) as claimed in claim 1, wherein the electronics housing (3) has a charging interface which is connected to a power store (21) of the endoscope (1) and is accessible from outside.

14. The endoscope (1) as claimed in claim 1, further comprising at least one of an image data processor (22) or control electronics (23) for the light source (7) assigned to the optical waveguide (5).

15. The endoscope (1) as claimed in claim 1, further comprising an image sensor (24) arranged in the distal end (6) of the endoscope shaft (2) or in the electronics housing (3) and sealed off in a vapor-tight and liquid-tight manner.

16. The endoscope (1) as claimed in claim 15, wherein the image sensor (24) is arranged adjacent to a proximal end (25) of the endoscope shaft (2).

17. The endoscope (1) as claimed in claim 1, wherein transmission of an image from an examination space (26) into the electronics housing (3) takes place electronically via an image sensor (24) located in a distal end (6) of the endoscope shaft (2).

18. The endoscope (1) as claimed in claim 1, wherein transmission of an image from an examination space (26) into the electronics housing (3) takes place optically via an optical channel (28) that is connected to an image sensor (24) at a proximal end (25) of the endoscope shaft (2).

\* \* \* \* \*